(12) United States Patent
Schneider et al.

(10) Patent No.: US 9,597,235 B2
(45) Date of Patent: Mar. 21, 2017

(54) METHODS AND APPARATUSES FOR REJECTING DEFECTIVE ABSORBENT ARTICLES FROM A CONVERTING LINE

(71) Applicant: The Procter & Gamble Company, Cincinnati, OH (US)

(72) Inventors: Uwe Schneider, Cincinnati, OH (US); Robert George Cox, Jr., Cincinnati, OH (US); Michael Devin Long, Springfield Township, OH (US); Justin B. Owens, Fort Thomas, KY (US); Todd Douglas Lenser, Liberty Township, OH (US); David Carlton Ordway, Oxford, OH (US); Kazuya Ogawa, Akashi (JP); Jeffry Rosiak, Loveland, OH (US); Jeffrey Michael Kent, Lebanon, OH (US); Louis J. Cedrone, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 684 days.

(21) Appl. No.: 13/873,616

(22) Filed: Apr. 30, 2013

(65) Prior Publication Data

US 2013/0296148 A1 Nov. 7, 2013

Related U.S. Application Data

(60) Provisional application No. 62/640,831, filed on May 1, 2012.

(51) Int. Cl.
*B65G 47/22* (2006.01)
*A61F 13/49* (2006.01)
(Continued)

(52) U.S. Cl.
CPC ........ *A61F 13/49* (2013.01); *A61F 13/15764* (2013.01); *A61F 13/15772* (2013.01)

(58) Field of Classification Search
CPC ................ A61F 13/49; A61F 13/15764; A61F 13/15772; A61F 13/15577; B31B 2201/02; B65G 47/24
(Continued)

(56) References Cited

U.S. PATENT DOCUMENTS 1,429,093 A * 9/1922 Paranteau ................ A23N 3/00
198/482.1
3,802,547 A * 4/1974 Wagers, Jr. ............. A61J 3/074
198/411
(Continued)

FOREIGN PATENT DOCUMENTS

EP 0 812 789 A2 12/1997
EP 1 179 495 A1 2/2002
(Continued)

OTHER PUBLICATIONS

U.S. Appl. No. 13/434,984, filed Mar. 30, 2012, Schneider.
(Continued)

*Primary Examiner* — Andrew M Tecco
*Assistant Examiner* — Praachi M Pathak
(74) *Attorney, Agent, or Firm* — Charles R. Matson

(57) ABSTRACT

The present disclosure relates to methods and apparatuses for rejecting defective absorbent articles from a converting line. At a downstream portion of a converting process, a continuous length of absorbent articles may be subjected to a final knife and cut to create discrete absorbent articles advancing on a first carrier. From the first carrier, the discrete absorbent articles may be transferred to a transfer apparatus, which in turn, transfers the discrete absorbent articles to a second carrier. The transfer apparatus may include carrier (Continued)

members that orbit around an axis of rotation and may be adapted to receive the absorbent articles from the first carrier and transfer the absorbent articles to the second carrier. Defective absorbent articles may be detected by an inspection system, which may be operably connected with the transfer apparatus and/or the first carrier to remove the defective absorbent articles from the converting process.

7 Claims, 12 Drawing Sheets

(51) Int. Cl.
*B65G 47/34* (2006.01)
*A61F 13/15* (2006.01)

(58) Field of Classification Search
USPC ...... 49/3, 12, 14, 16, 19, 25, 405, 379, 378; 198/471.1, 377.04
See application file for complete search history.

(56) References Cited

U.S. PATENT DOCUMENTS

| | | | |
|---|---|---|---|
| 3,860,003 A | 1/1975 | Buell | |
| 4,519,596 A | 5/1985 | Johnson et al. | |
| 4,578,133 A | 3/1986 | Oshefsky et al. | |
| 4,610,678 A | 9/1986 | Weisman et al. | |
| 4,617,082 A | 10/1986 | Oshefsky et al. | |
| 4,650,173 A | 3/1987 | Johnson et al. | |
| 4,673,402 A | 6/1987 | Weisman et al. | |
| 4,695,278 A | 9/1987 | Lawson | |
| 4,704,115 A | 11/1987 | Buell | |
| 4,715,846 A | 12/1987 | Zak | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 4,913,691 A * | 4/1990 | Chaygneaud-Dupuy . | B31B 1/02 198/689.1 |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,745,922 A | 5/1998 | Rajala et al. | |
| 5,916,661 A | 6/1999 | Benson et al. | |
| 6,107,539 A | 8/2000 | Palumbo et al. | |
| 6,165,306 A * | 12/2000 | Rajala ............... | A61F 13/15764 156/263 |
| 6,248,195 B1 | 6/2001 | Schmitz | |
| 6,250,357 B1 | 6/2001 | Niedermeyer | |
| 6,319,347 B1 | 11/2001 | Rajala et al. | |
| 6,545,197 B1 | 4/2003 | Muller et al. | |
| 6,546,987 B1 | 4/2003 | Tachibana et al. | |
| 6,790,798 B1 | 9/2004 | Suzuki et al. | |
| 6,869,386 B2 * | 3/2005 | Lamping ............ | G05B 19/41815 493/3 |
| 6,900,450 B2 * | 5/2005 | Gimenez ............ | A61F 13/15756 250/559.29 |
| 7,383,865 B2 | 6/2008 | Umebayashi et al. | |
| 7,569,039 B2 | 8/2009 | Matsuda et al. | |
| 7,587,966 B2 | 9/2009 | Nakakado et al. | |
| 7,809,179 B2 * | 10/2010 | Singh ................ | A61F 13/15772 348/92 |
| 8,011,493 B2 | 9/2011 | Giuliani et al. | |
| 8,145,338 B2 | 3/2012 | Kent et al. | |
| 8,720,666 B2 * | 5/2014 | Papsdorf ............ | A61F 13/15764 198/377.01 |
| 2002/0055430 A1 * | 5/2002 | Coenen ................ | B65D 5/6602 493/59 |
| 2004/0094050 A1 | 5/2004 | Ackley, Jr. et al. | |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2008/0223537 A1 | 9/2008 | Wiedmann | |
| 2009/0312730 A1 | 12/2009 | LaVon et al. | |
| 2010/0012285 A1 | 1/2010 | Wiedmann | |
| 2010/0305740 A1 | 12/2010 | Kent et al. | |
| 2012/0021186 A1 | 1/2012 | Schneider | |
| 2012/0061015 A1 | 3/2012 | LaVon et al. | |
| 2012/0061016 A1 | 3/2012 | LaVon et al. | |
| 2012/0145314 A1 * | 6/2012 | Piantoni ............ | A61F 13/15764 156/256 |
| 2013/0001042 A1 | 1/2013 | Yamamoto | |
| 2013/0296148 A1 * | 11/2013 | Schneider ............ | A61F 13/49 493/3 |
| 2015/0250655 A1 * | 9/2015 | Kawka ............... | A61F 13/15764 156/64 |

FOREIGN PATENT DOCUMENTS

| | | |
|---|---|---|
| EP | 1 820 757 A1 | 8/2007 |
| EP | 2 522 603 A1 | 11/2011 |
| JP | 2003-135517 A | 5/2003 |

OTHER PUBLICATIONS

U.S. Appl. No. 13/447,531, filed Apr. 16, 2012, Papsdorf, et al.
U.S. Appl. No. 13/873,603, filed Apr. 30, 2013, Schneider, et al.
International Search Report, PCT/US2013/038985, dated Jun. 14, 2013, 8 pages.

* cited by examiner

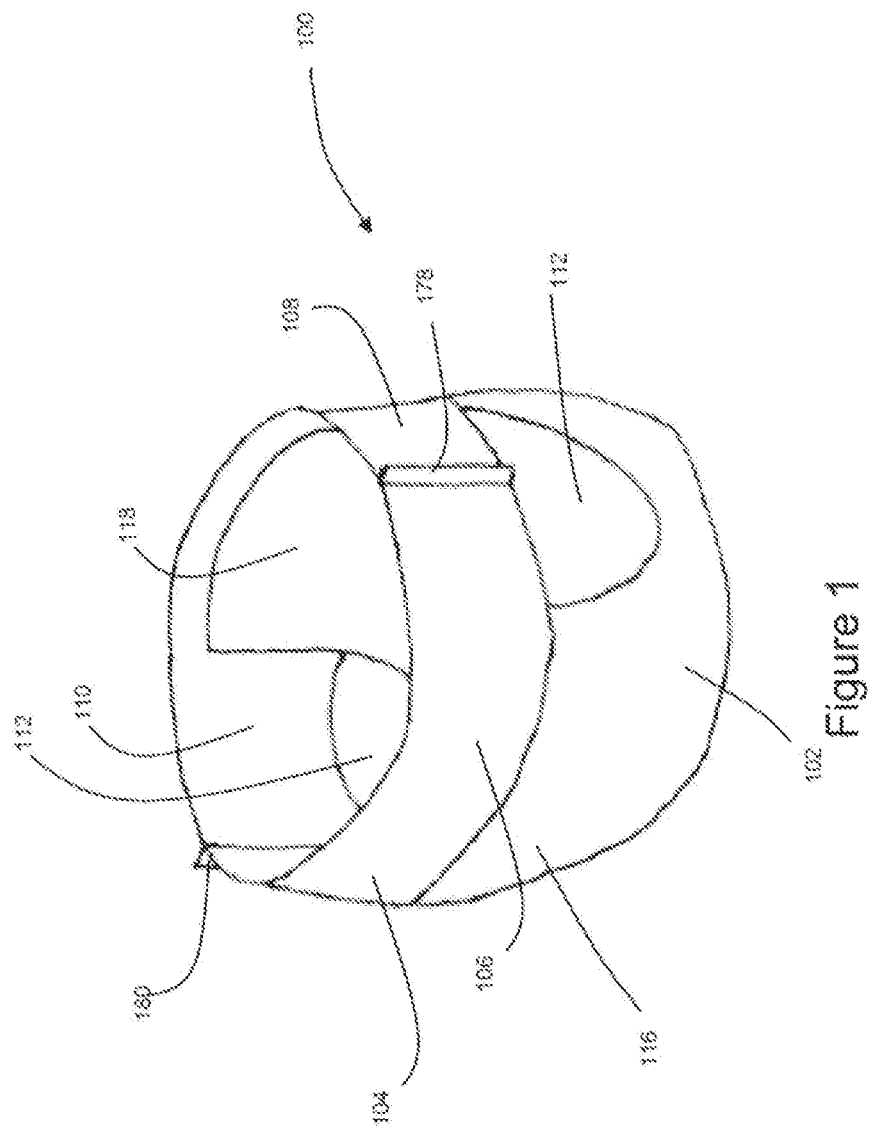

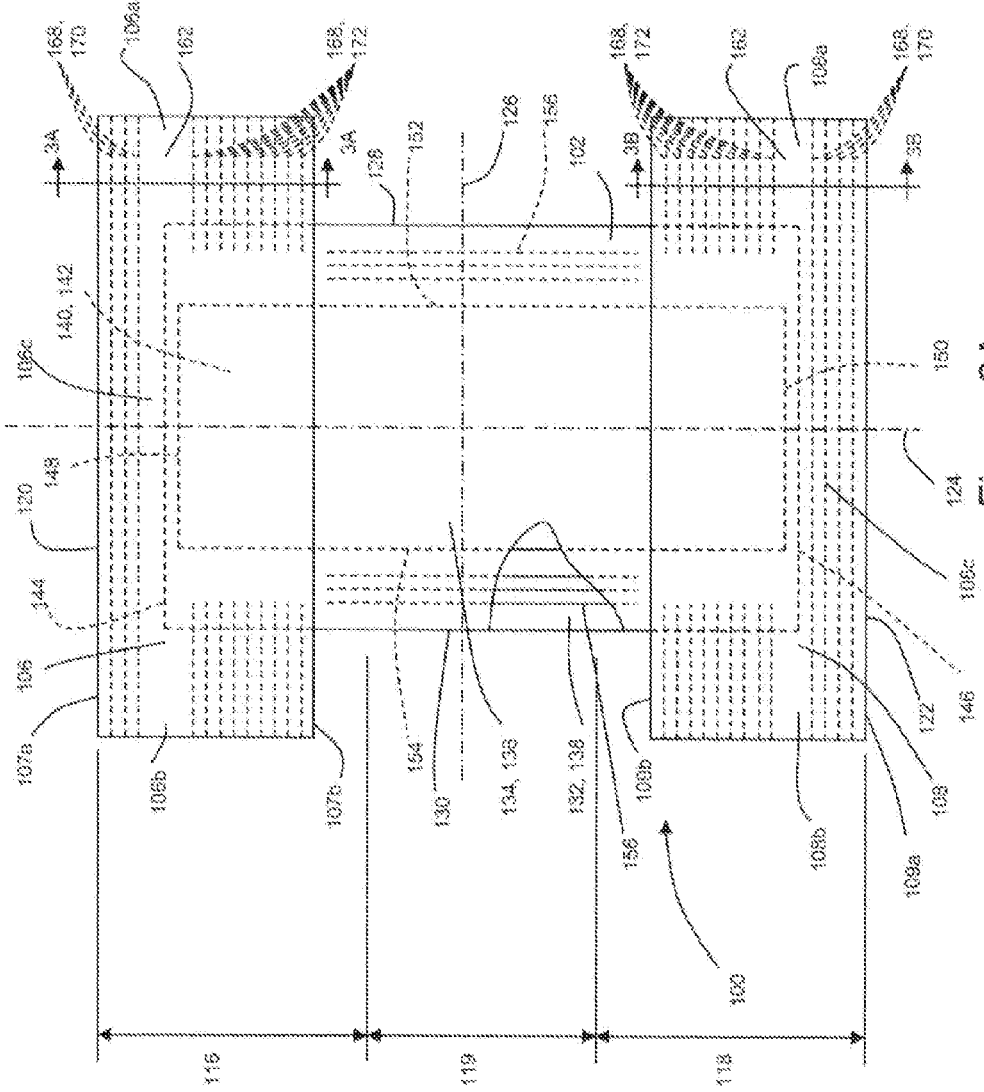
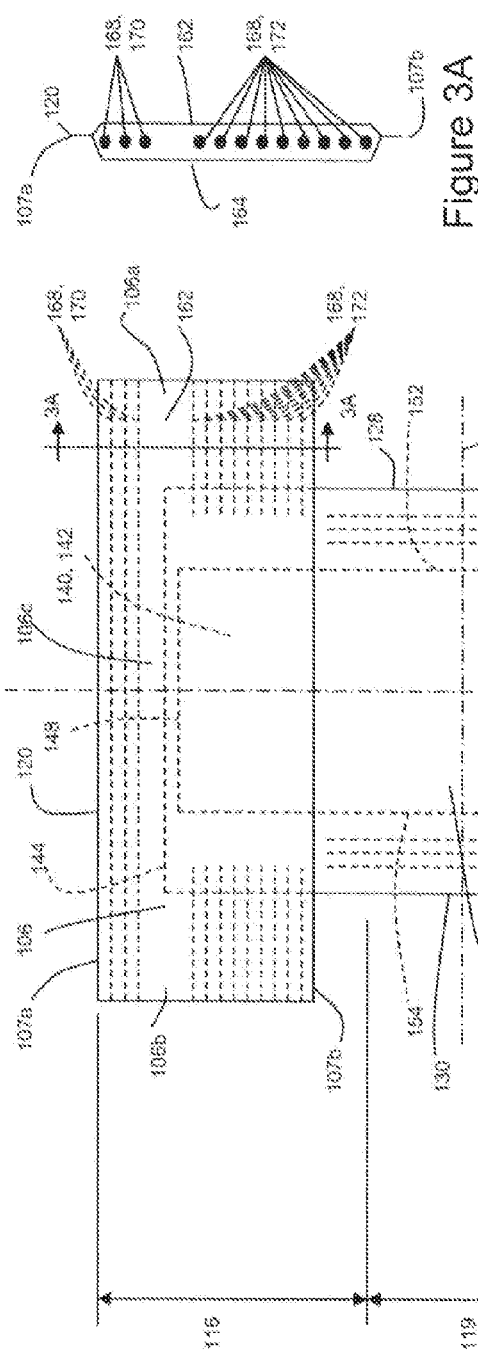
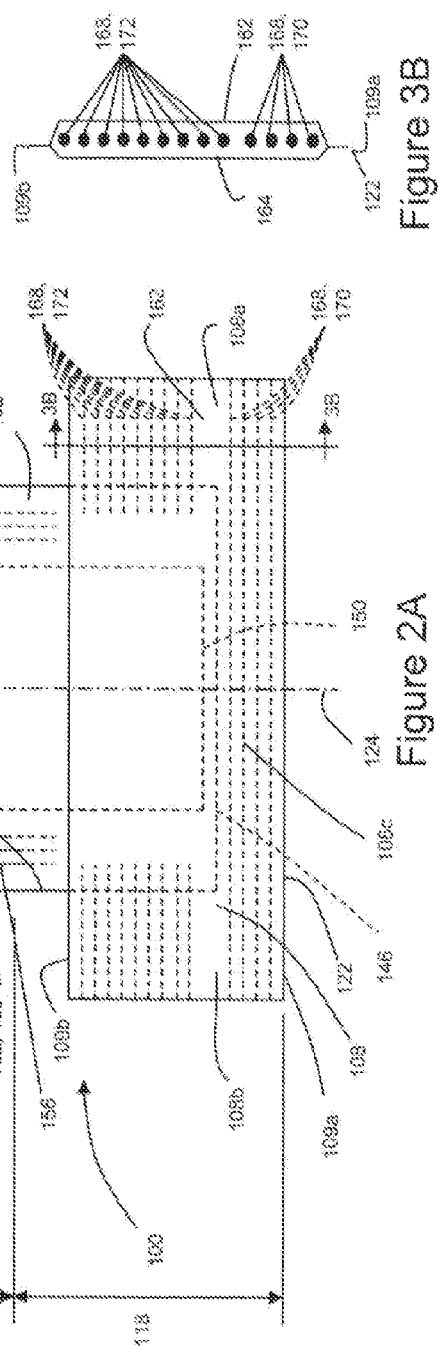

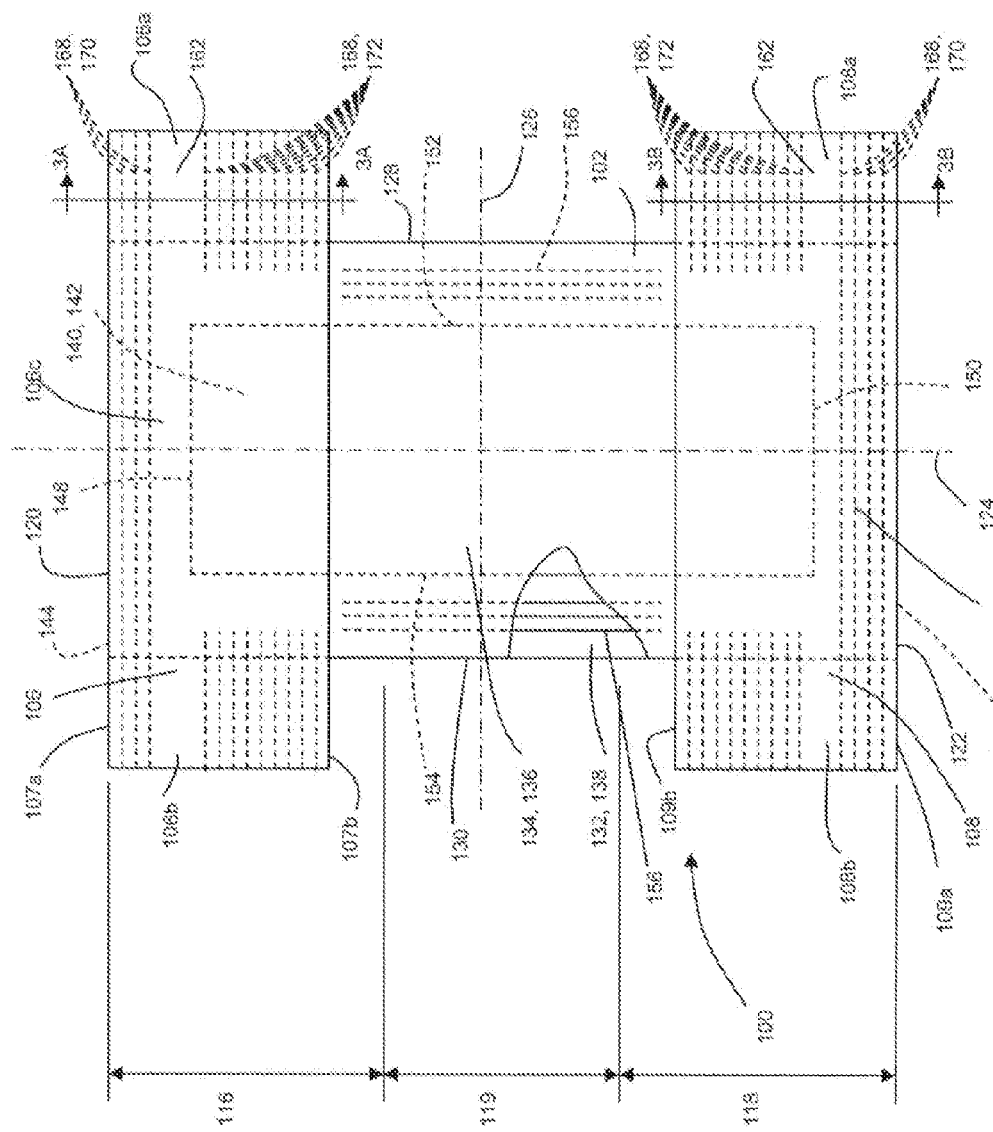

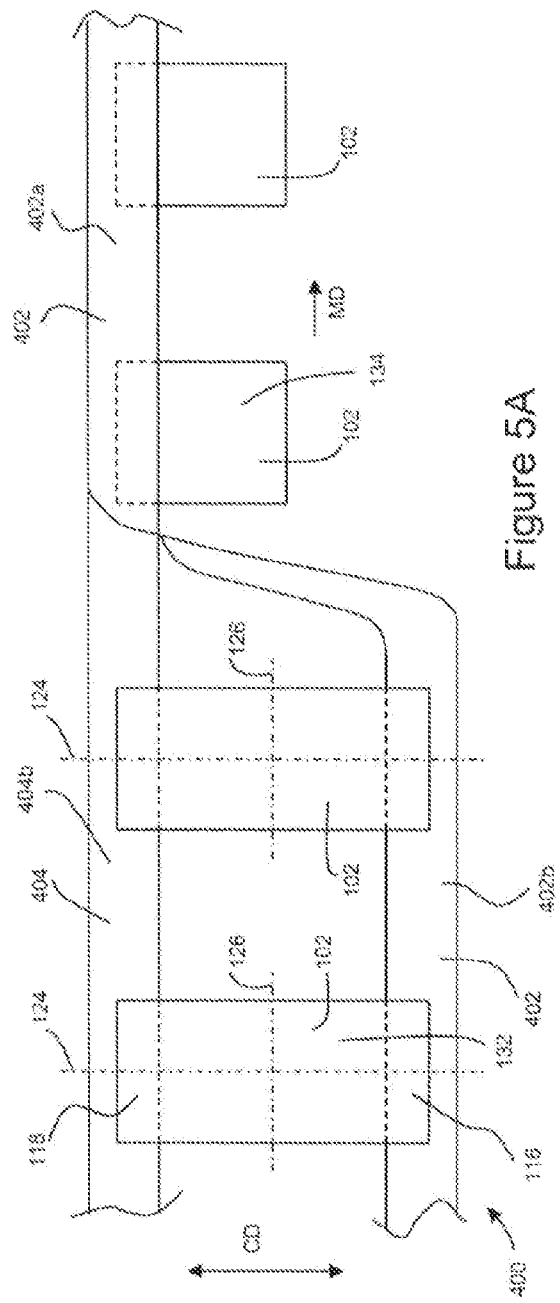
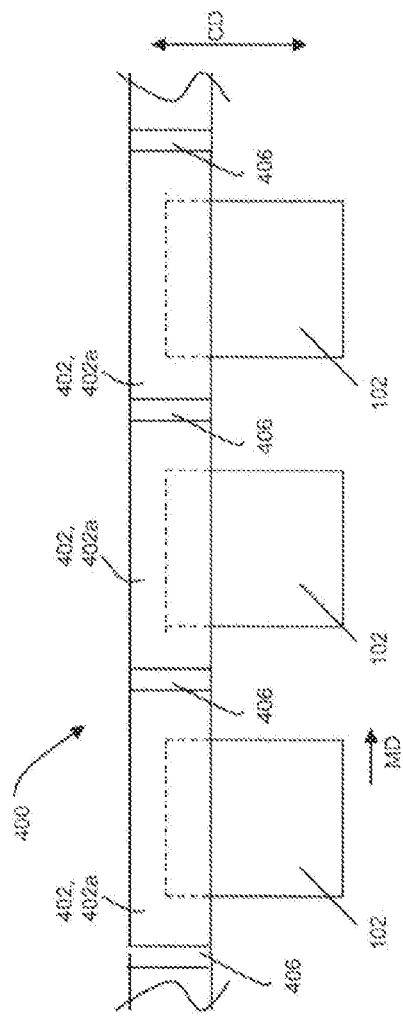

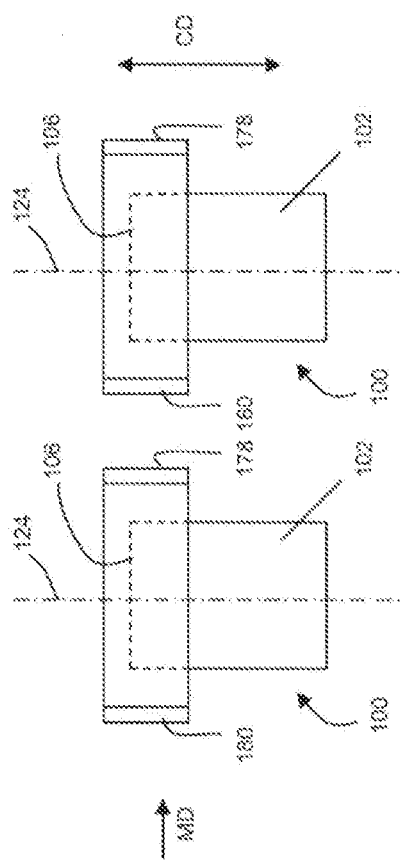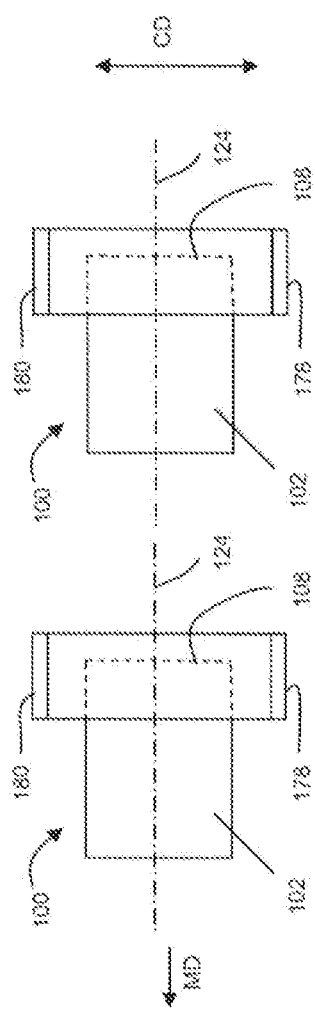

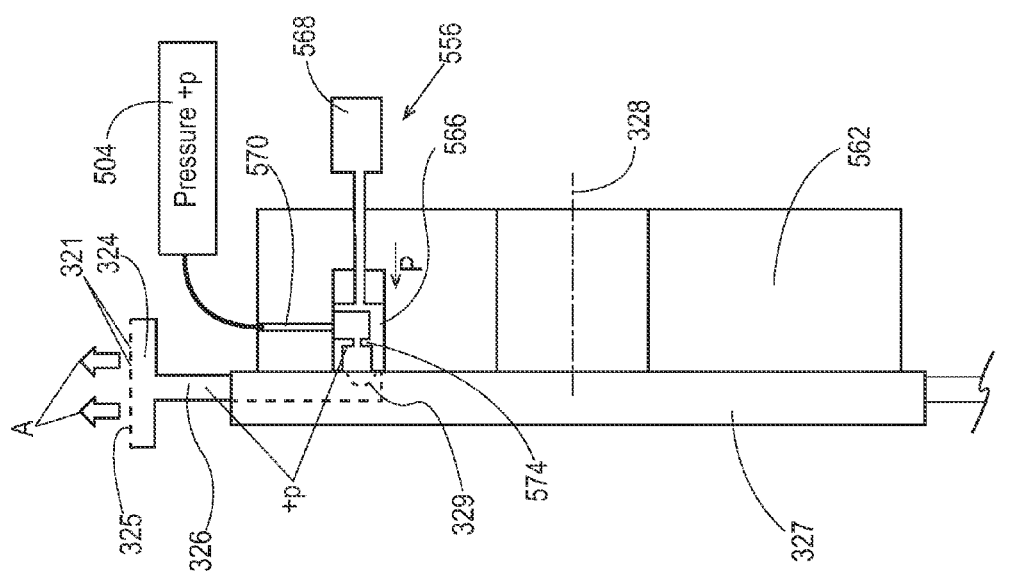
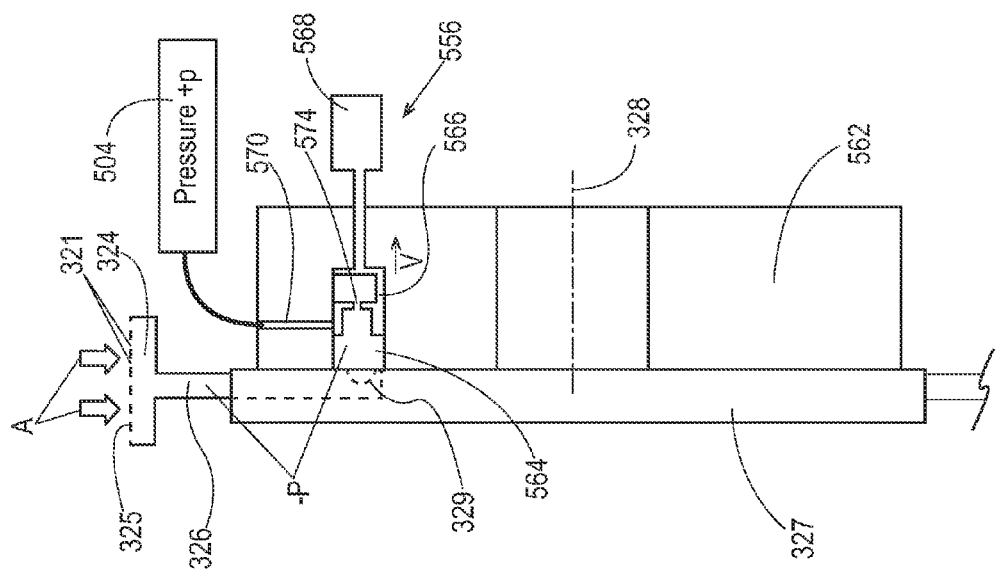

METHODS AND APPARATUSES FOR REJECTING DEFECTIVE ABSORBENT ARTICLES FROM A CONVERTING LINE

FIELD OF THE INVENTION

The present disclosure relates to systems and methods for manufacturing disposable absorbent articles, and more particularly, systems and methods for detecting and rejecting defective absorbent articles from a converting line.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

For quality control purposes, absorbent article converting lines may utilize various types of sensors to detect defects in the webs and discrete components added to the webs along the converting line as absorbent articles are constructed. Example sensor technology may include vision systems, photoelectric sensors, proximity sensors, laser or sonic distance detectors, and the like. Sensor data may be communicated to a controller. In turn, the controller may be programmed to receive sensor data and reject or cull defective diapers after the final knife cut at the end of the converting line.

Various systems are used for rejecting defective diapers, such as by diverting the defective diapers from the stream of diapers that are of satisfactory condition or good quality. For example, one system that has been used to reject cut web products includes forcing the defective diapers out of the stream of satisfactory products by using pneumatic air blasts, which divert the defective diapers to a path that differs from that for the stream of satisfactory diapers. In such a method, the defective diapers are detected, and a pneumatic air blast from one or more nozzles forces the defective diapers out of the stream of quality products and into a reject bin provided in proximity of the conveyor system or production line. Such existing systems of rejecting cut web products using pneumatic air blasts may have some disadvantages. For example, a separate system having pneumatic nozzles and associated hoses and/or piping require space, such as for example, extra space along the conveyor system. In addition, such systems may not be entirely accurate and can divert more than solely the defective diapers from the stream of satisfactory products.

Other methods of rejecting defective diapers may include mechanically activated switches, or flippers, that divert the defective cut web products to an alternative pathway, similar to the manner railway switches can divert trains to a different track. The mechanical switches are may be activated via a pneumatic or hydraulic cylinder or via an electric motor. Some configuration may include mechanical switches that pop up from the conveyor system and divert the defective diapers below the switch and toward an alternate pathway. With such mechanically operated systems, more space may be required to accommodate the mechanically activated switches. Thus, space consumption is a disadvantage to the mechanical switch method. Furthermore, the additional mechanical switch equipment may result in added complexity and cost.

Consequently, it would be beneficial to provide a relatively less complex and less spacious system for high speed selective redirecting and/or rejecting of absorbent articles. In addition, a method and apparatus that is relatively more accurate in removing only the defective absorbent articles from the stream of quality products may also be desirable. Further, a system that utilizes some existing converting equipment and control mechanisms to reject products rather than a completely separate system to perform redirecting and/or rejecting operations may be desirable.

SUMMARY OF THE INVENTION

The present disclosure relates to methods and apparatuses for rejecting defective absorbent articles from a converting line. At a downstream portion of a converting process, a continuous length of absorbent articles may be subjected to a final knife and cut to create discrete absorbent articles advancing on a first carrier. From the first carrier, the discrete absorbent articles may be transferred to a transfer apparatus, which in turn, transfers the discrete absorbent articles to a second carrier. The transfer apparatus may include carrier members that orbit around an axis of rotation and may be adapted to receive the absorbent articles from the first carrier and transfer the absorbent articles to the second carrier. Defective absorbent articles may be detected by an inspection system, which may be operably connected with the transfer apparatus and/or the first carrier to remove the defective absorbent articles from the converting process.

A method for rejecting defective absorbent articles from a web converting manufacturing process may include the steps of: converting a substrate and component parts into a continuous length of absorbent articles; inspecting the substrate or component parts with a sensor; communicating inspection parameters from the sensor to a controller; cutting the continuous length of absorbent articles into discrete absorbent articles; identifying defective discrete absorbent articles based on the inspection parameters; advancing the discrete absorbent articles in a machine direction on a first carrier; applying a vacuum pressure to the first carrier to hold the discrete absorbent articles on the first carrier; transferring discrete absorbent articles from the first carrier onto carrier members at a pick-up zone proximate the first carrier; moving carrier members from the first position proximate the first carrier to a second position proximate a second carrier; and transferring discrete absorbent articles from the carrier members to the second carrier at a drop off zone; and rejecting defective discrete absorbent articles before the defective absorbent articles are transferred to the carrier members.

A system for rejecting defective absorbent articles may include: a first carrier including a carrier surface having a plurality of apertures; a second carrier; a carrier member adapted to orbit about a first axis of rotation, the carrier member adapted to pick up an absorbent article from the first carrier in a pick-up zone and transfer the absorbent article to the second carrier in a drop off zone; a vacuum air system in fluid communication with apertures in the carrier surface along a first length of the first carrier; a valve body in fluid communication with apertures in the carrier surface along a second length of the first carrier; an insert operably connected with the valve body; and an actuator connected with the insert and adapted to rotate the insert to a first position and a second position, wherein apertures in the second length are in fluid communication with the vacuum air system when the insert is in the first position, and wherein apertures in the second length are not in fluid communication with the vacuum system when the insert is in the second position.

BRIEF DESCRIPTION OF THE DRAWINGS

FIG. 1 is a perspective view of a diaper pant.

FIG. 2A is a partially cut away plan view of the diaper pant shown in FIG. 1.

FIG. 2B is a partially cut away plan view of a second embodiment of a diaper pant.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 5A is a view of multiple discrete chassis connected with front and back side panel material and being folded to place the front and back side panel material in a facing relationship from FIG. 4 taken along line 5A-5A.

FIG. 5B is a view of folded multiple discrete chassis with the front and back side panel material in a facing relationship from FIG. 4 taken along line 5B-5B.

FIG. 5C is a view of two discrete absorbent articles oriented such that the longitudinal axis is generally perpendicular to the machine direction MD from FIG. 4 taken along line 5C-5C.

FIG. 5D is a view of two discrete absorbent articles oriented such that the longitudinal axis is generally parallel with the machine direction MD from FIG. 4 taken along line 5D-5D.

FIG. 10A is a cross sectional view of a pneumatic system and manifold valve assembly operably connected with the transfer apparatus in a first mode of operation from FIG. 9 taken along line 10-10.

FIG. 10B is a cross sectional view of a pneumatic system and manifold valve assembly operably connected with the transfer apparatus in a second mode of operation from FIG. 9 taken along line 10-10.

DETAILED DESCRIPTION OF THE INVENTION

Figure 4:
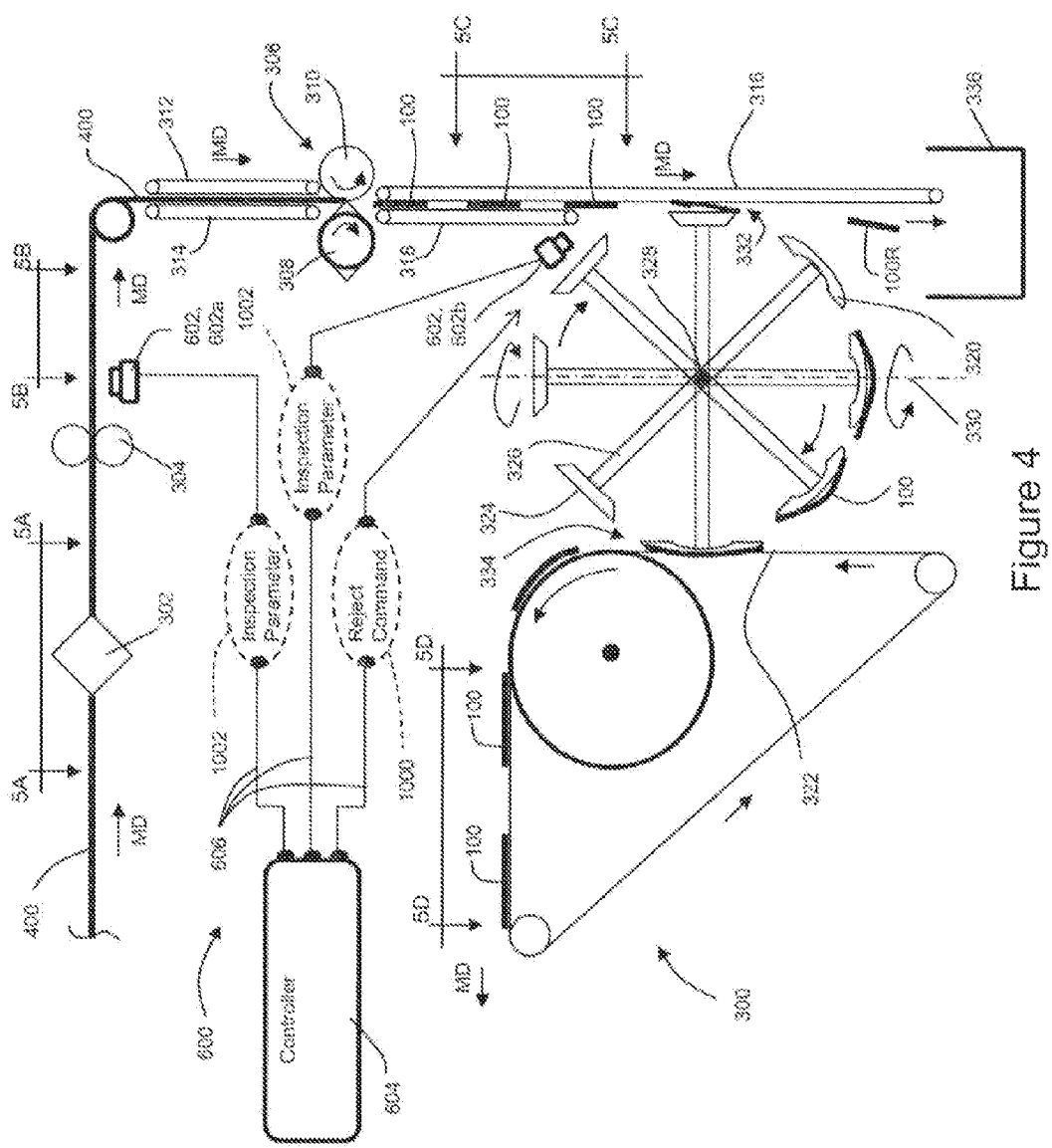
FIG. 4 is a schematic side view of a converting apparatus adapted to manufacture diapers.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a defined woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed.

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The present disclosure relates to methods and apparatuses for manufacturing absorbent articles, and more particularly, systems and methods for detecting and rejecting defective absorbent articles from a converting line. As discussed in more detail below, during the converting process, various continuous substrates and/or discrete components may be combined with each other to form a continuous length of absorbent articles. At a downstream portion of the converting process, the continuous length of absorbent articles may be subjected to a final knife and cut to create separate and discrete absorbent articles in the form of diapers. The discrete absorbent articles may then advance in a machine direction MD in a first orientation on a first carrier. From the first carrier, the discrete absorbent articles are transferred to a transfer apparatus. The transfer apparatus, in turn, transfers the discrete absorbent articles to a second carrier in a second orientation that is different from the first orientation. More particularly, the transfer apparatus rotates around an axis of rotation, and may include carrier members that orbit around the axis of rotation. The carrier members are adapted to receive the absorbent articles in the first orientation from the first carrier and transfer the absorbent articles to the second carrier in the second orientation. As such, the absorbent articles may be transferred in a first orientation from the first carrier to the carrier members in a pick-up zone, and the absorbent articles may be transferred in a second orientation from the carrier members to the second carrier in a drop-off zone. As discussed in more detail below, defective absorbent articles may be detected and tracked by an inspection system. In turn, the inspection system may be operably connected with the transfer apparatus and/or the first carrier to remove the defective absorbent articles from the converting process. Absorbent articles that are not deemed to be defective may be transferred to the second carrier from the transfer apparatus and subject to further processing steps, such as for example, side panel tucking and packaging operations.

As discussed in more detail below, the inspection system may be configured to operate with the transfer apparatus and/or first carrier in various ways to remove defective absorbent articles from the manufacturing process. In some embodiments, the first carrier may include a vacuum source that applies suction forces to hold the absorbent articles to the first carrier as the absorbent articles advance to the pick-up zone. The first carrier may also include a positive pressure source that "blows-off" or pushes the absorbent articles away from the first carrier at or downstream of the pick-up zone. Further, the carrier members on the transfer apparatus may be fluidly connected with a vacuum source that applies suction forces to hold the absorbent articles on the carrier members while moving from the first carrier to the second carrier. As such, the inspection system may be operably connected with vacuum and/or positive pressures systems associated with the transfer apparatus and/or the first carrier to reject and redirect defective absorbent articles from the converting process.

In some configurations, the inspection system may be configured to reject defective absorbent articles after the defective absorbent articles have been transferred to a carrier member on the transfer apparatus. For example, the inspection system may be operable to temporarily disconnect the vacuum system from the carrier member holding the defective absorbent article. As such, the defective absorbent article is no longer held to the carrier member with suction forces, and in turn, may be channeled or redirected from the carrier member to a reject bin. In some embodiments, the inspection system may be operable to disconnect the vacuum source and then temporarily connect a positive air pressure source with the carrier member holding the defective article. As such, the positive air pressure source acts to push or "blow-off" the defective absorbent article from the carrier member.

In some embodiments, the inspection system may be configured to reject defective absorbent articles by preventing the defective absorbent articles from being transferred to the carrier members on the transfer apparatus. For example, the inspection system may be operable to temporarily disengage the vacuum system from the carrier member near or at the pick-up zone before the carrier member picks up a defective absorbent article from the first carrier. In addition, the inspection system may be operable to maintain the vacuum system connection with the first carrier in the pick-up zone. As such, suction forces from the vacuum system continue to hold the defective absorbent article on the first carrier as the defective absorbent article advances into the pick-up zone. In addition, suction forces may be maintained to the hold the defective absorbent article on the first carrier as the defective absorbent article advances past the pick-up zone.

It is to be appreciated that with respect to the transfer apparatus, the first orientation and the second orientation may be described in various ways. For example, as discussed in more detail below, the first orientation may be described by reference to some physical aspect or component of an advancing absorbent article relative to the machine direction MD or cross direction CD. In some embodiments, the first orientation may be described as having a longitudinal axis of each absorbent article oriented in a cross direction CD or being perpendicular or generally perpendicular to the machine direction MD. As mentioned above, the absorbent articles may then advance to the transfer apparatus that positions the advancing absorbent articles in a second orientation. The second orientation may for example be described as having the advancing absorbent articles being turned by some angle with respect to the first orientation, such as for example, having been turned 90° or 180° with respect to the first orientation. In some embodiments, the second orientation may be described as having the longitudinal axis of each advancing absorbent article oriented so as to be parallel or generally parallel with the machine direction MD.

It is to be appreciated that although the methods and apparatuses herein may be configured to reject various types of products, the methods and apparatuses herein are discussed below in the context of manufacturing absorbent articles. In particular, the methods and apparatuses are discussed in the context of rejecting advancing, defective diapers during production.

FIGS. 1 and 2A show an example of a diaper pant 100 that may be assembled and folded in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 120 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 120 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 120 in the front waist region 116 and the laterally extending back waist edge 122 in the back waist region 118. When the diaper pant 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; and 4,704,115; and U.S. Patent Publication No. 2009/0312730A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172.

As shown in FIG. 2A, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2A, the inner, waist elastics 172 extend intermittently along the first and second elastic belts 106, 108. More particularly, the inner, waist elastics 172 extend along the first and second opposing end regions 106*a*, 106*b* and partially across the central region 106*c* of the first elastic belt 106. The inner, waist elastics 172 also extend along the first and second opposing end regions 108*a*, 108*b* and partially across the central region 108*c* of the second elastic belt 108. As such, the inner, waist elastics 172 do not extend across the entirety of the central regions 106*c*, 108*c* of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107*a* of the first elastic belt 106, and the second laterally extending end edge 146 is aligned along and coincides with the outer lateral edge 109*a* of the second belt 108.

As previously mentioned, the inspection methods and systems according to the present disclosure may be utilized during the assembly of various components of diapers 100. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1 and 2A. Although the following methods are provided in the context of the diaper 100 shown in FIGS. 1 and 2A, it is to be appreciated that various embodiments of diapers can be manufactured according the methods disclosed herein, such as for example, the absorbent articles disclosed in U.S. Pat. Nos. 7,569,039 and 5,745,922; U.S. Patent Publication Nos. 2005/0107764A1, 2012/0061016A1, and 2012/0061015A1, which are all hereby incorporated by reference herein.

FIG. 4 shows an example converting apparatus 300 that may operate in conjunction with an inspection system configured to remove defective articles from the manufacturing process. The converting apparatus operates to advance a continuous length of absorbent articles 400 including discrete chassis 102 connected with continuous lengths of advancing first and second elastic belt substrates 402, 404 along a machine direction MD. As discussed in more detail below, portions of the first belt substrate may be converted to correspond with the first elastic belt 106 and portions of the second belt substrate may be converted to correspond with the second elastic belt 108 discussed above with reference to FIGS. 1-3B. As shown in FIGS. 4 and 5A, the first belt substrate 402 includes a first, garment facing, surface 402*a* and an opposing second, wearer facing, surface 402*b*. And the second belt substrate 404 a first, garment facing, surface 404*a* and an opposing second, wearer facing, surface 404*b*. The lateral axis of each chassis 102 is parallel with the machine direction MD, and the longitudinal axis of each chassis is perpendicular with the machine direction MD. The chassis 102 are also spaced apart from each other along the machine direction. Opposing waist regions 116, 118 of the spaced apart chassis 102 are connected with continuous lengths of advancing first and second elastic belt substrates 402, 404.

It is to be appreciated that FIG. 4 illustrates an example a downstream portion of a converting process configured to assemble a continuous length of absorbent articles by combining various continuous substrates and/or discrete components with each other. It is to be appreciated the apparatus of FIG. 4 can be configured to work with various configurations of converting systems, such as for example those disclosed in U.S. patent application Ser. No. 13/434,984, entitled "Apparatuses and Methods for Making Absorbent Articles," filed on Mar. 30, 2012.

As shown in FIGS. 4 and 5A, the continuous length of absorbent articles 400 advances to a folding apparatus 302. At the folding apparatus 302, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis 102 also positions the wearer facing surface 402*b* of the first belt substrate 402 extending between each chassis 102 in a facing relationship with the wearer facing surface 404*b* of the second belt substrate 404 extending between each chassis 102.

As shown in FIGS. 4 and 5B, the folded discrete chassis 102 connected with the first and second belt substrates 402, 404 are advanced from the folding apparatus 302 to a bonder 304. The bonder 304 operates to bond a portion of the second belt substrate 404 extending between each chassis 102 with a portion of the first belt substrate 402 extending between each chassis 102, thus creating discrete bond regions 406. It is to be appreciated that various types of bonder apparatuses and methods can be used to bond the second belt substrate material 404 with the first belt substrate material 402, such as for example disclosed in U.S. Pat. Nos. 6,248,195; 6,546,987; and 7,383,865, as well as U.S. Patent Publication No. 2012/0021186A1, which are incorporated by reference herein.

With continued reference to FIG. 4, the continuous length of absorbent articles 400 are advanced from the bonder 304 to a cutting apparatus 306 including a knife roll 308 and anvil roll 310. The cutting apparatus cuts the discrete bond regions 406 are cut along the cross direction CD to create a first side seam 178 on an absorbent article 100 and a second side seam 180 on a subsequently advancing absorbent article. As such, the elastic belt substrates 402, 404 are cut along the seams 406 to create discrete diapers 100, such as shown in FIG. 1. As shown in FIG. 4, the apparatus 300 may include opposing first and second belt conveyors 312, 314 that help hold the continuous length of absorbent articles 400 in position while advancing to the cutting apparatus 306.

From the cutting apparatus 306, a first carrier 316 may advance the discrete diapers 100 in the machine direction MD in a first orientation to a transfer apparatus 320. With continued reference to FIGS. 4 and 5C, the discrete diapers 100 are transferred from the first carrier 316 in a first orientation to the transfer apparatus 320. In turn, the transfer apparatus 320 moves the discrete diapers 100 in the first orientation from the first carrier 316, orients the diapers 100 into a second orientation, and transfers the articles 100 to a second carrier 322 in the second orientation, such as shown in FIG. 5D. From the second carrier 322, the discrete diapers 100 may be subjected to further processing steps, such as for example, side panel tucking and/or packaging operations.

As discussed above, the converting apparatus 300 may be configured to construct and arrange the discrete diapers 100 in various positions or orientations before being transferred to the transfer apparatus 320, and as such, various representations of first orientations may be described in various ways. For example, as shown in FIG. 5C, the advancing discrete diapers 100 are shown in a first orientation wherein the longitudinal axis 124 of each absorbent article 100 is oriented in a cross direction CD. In FIG. 5C, the first orientation may also be described as having the longitudinal axis 124 perpendicular or generally perpendicular to the machine direction MD. The discrete articles 100 are transferred to the transfer apparatus 320 and then transferred to a second carrier 322 in a second orientation. As discussed above with reference to the first orientation, the second orientation may be described in various ways. For example, as shown in FIG. 5D, the advancing discrete diapers 100 are shown in a second orientation wherein the longitudinal axis 124 of each advancing absorbent article 100 is oriented so as to be parallel or generally parallel with the machine direction MD. The second orientation may also be described with reference to the first orientation. For example, the diapers 100 in the second orientation may be described as having been turned by an angle relative to the diapers 100 in the first orientation, such as 90°.

It is to be appreciated that various components of the converting apparatus 300 have various configurations. For example, although the first carrier 316 and the second carrier are depicted as belt conveyors in FIG. 4, it is to be appreciated that the first carrier 316 and/or the second carrier 322 may be configured in various ways. For example, in some embodiments, the first carrier 316 and/or second carrier 322 may be configured as a rotating drum. In order to help mitigate problems associated with uncontrolled movement of the discrete diapers 100 during conveyance, the first carrier 316 and/or second carrier 322 may also include a vacuum system in communication with a porous and/or apertured belt or other foraminous carrier surface 317, 323 that allows the suction force of the vacuum system to be exerted on diapers 100. As discussed below with reference to FIG. 6, a pneumatic system 500, including a vacuum system 502 and a positive pressure system 504, may be fluidly connected with the porous and/or apertured carrier surface 317 of the first carrier 322. The vacuum system 502 may operate to apply a suction force to help hold the discrete diapers 100 on the carrier surface 317, and the positive pressure system 504 may operate to apply positive pressure force to blow-off or push the discrete diapers 504 away from the carrier surface 317. As discussed in more detail below, the pneumatic system 500 may also be adapted to work with an inspection system to remove defective diapers 100R from the converting process. Referring back to FIG. 4, a belt conveyor 318 may also be positioned adjacent the first carrier 316 to help hold the discrete diapers 100 flat against the first carrier 316.

As shown in FIG. 4, the transfer apparatus 320 may include one or more carrier members 324 connected with support members 326 and adapted to rotate or orbit about a first axis of rotation 328. For example, the transfer apparatus 320 embodiment shown in FIG. 4 rotates clockwise around the first axis of rotation 328. The carrier members 324 may be adapted to pivot about a second axis 330 while moving or orbiting from an article pick-up zone 332 adjacent the first carrier 316 to an article drop-off zone 334 adjacent the second carrier 322. As such, each advancing discrete diaper 100 may be transferred in the pick-up zone 332 from the first carrier 316 in a first orientation to a carrier member 324. More particularly, the diaper 100 may be transferred onto a carrier surface 325 of the carrier member 324. As the transfer apparatus 320 rotates, the carrier member 324 and the diaper 100 move from the pick-up zone 332. As the carrier member 324 moves from the pick-zone to orbit around the first axis of rotation 328, the carrier member 324 pivots around the second axis 330 to orient the diaper 100 into the second orientation. It is to be appreciated that the carrier member 324 may pivot by various degrees of rotation around the second axis 330, such as for example 90° or 180°, while moving from the pick-up zone 332 to the drop-off zone 334. The carrier member 324 continues to orbit around the first axis of rotation 328 and the diaper 100 is transferred to the second carrier 322 in the drop-off zone 334 in the second orientation.

It is to be appreciated that various transfer apparatus configurations may utilized, such as for examples, the transfer apparatuses disclosed in U.S. patent application Ser. No. 13/447,531; U.S. Pat. Nos. 4,578,133; 4,617,082; 6,319,347; 7,341,047; 7,587,966; and 8,011,493; European Patent Publications EP0812789A2; EP1179495A1; and EP1820757A1; and European Patent Application No. EP12162251.8. It is also to be appreciated that the transfer apparatus 320 can be configured to increase or decrease the speed and/or spacing of the articles traveling from the first carrier 316 to the second carrier 322. It is also to be appreciated that in some embodiments, the carrier member 324 may not pivot about the second axis 324.

As discussed below with reference to FIG. 6, a pneumatic system 550, including a vacuum system 552 and a positive pressure system 554, may be fluidly connected with a porous and/or apertured carrier surface 325 of each carrier member 324. The vacuum system 552 may operate to apply a suction force to help hold the discrete diapers 100 on the carrier surface 552, and the positive pressure system 554 may operate to apply a positive pressure force to blow-off or push the discrete diapers 554 away from the carrier surface 325. As such, the vacuum system 552 may apply a suction force against the diapers 100 in a radially inward direction relative to the first axis of rotation 328, and the positive pressure system 552 may apply a pushing or blow-off force in a radially outward direction relative to the first axis of rotation 328. In some embodiments, the vacuum system 552 may be configured to apply a suction force to the diapers 100 in the pick-up zone 332 and cease applying the suction force to the diapers 100 in the drop-off zone 334. In some configurations, the positive pressure system may be operated at the drop-off zone 334 to apply a pushing or blow-off force to help remove the diapers 100 from carrier surface 325 of the carrier members 324. As discussed in more detail below, the pneumatic system 550 may also be adapted to work with an inspection system to remove defective diapers 100R from the carrier members 324 before being carried to the drop-off zone 334.

As previously mentioned, the first carrier 316 may include a porous and/or apertured carrier surface 317, and each carrier member 324 may include a porous and/or apertured carrier surface 325. For example, the embodiment of the first carrier 316 shown in FIGS. 7A-8B has a carrier surface 317 that may include a plurality of apertures 319. And the embodiment of the carrier member 324 shown in FIGS. 10A-11 has a carrier surface 325 that may include a plurality of apertures 321. As previously mentioned, the apparatus 300 may include a pneumatic system 500 in fluid communication with the carrier surface 317 of the first carrier 316, and/or a pneumatic system 550 in fluid communication with the porous and/or apertured carrier surface 325 of each carrier member 324 on the transfer apparatus 320. As such, it is to be appreciated that various types of pneumatic configurations may be used to selectively apply vacuum pressure and/or air pressure to the first carrier 316 and/or the carrier members 324.

Figure 6:
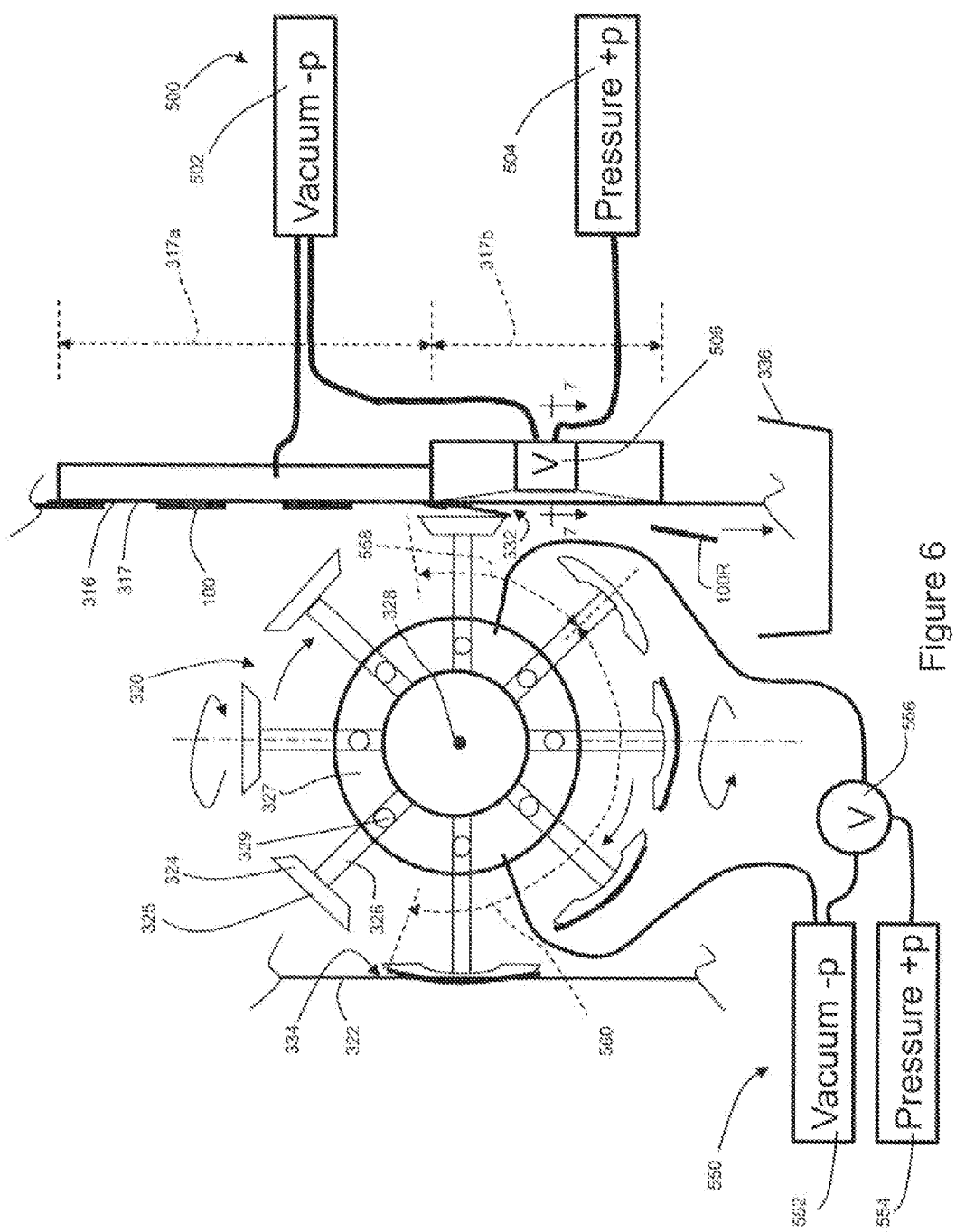
FIG. 6 is a detailed schematic view of an embodiment a first carrier and carrier apparatus along with associated pneumatic systems.
Figure 7A:
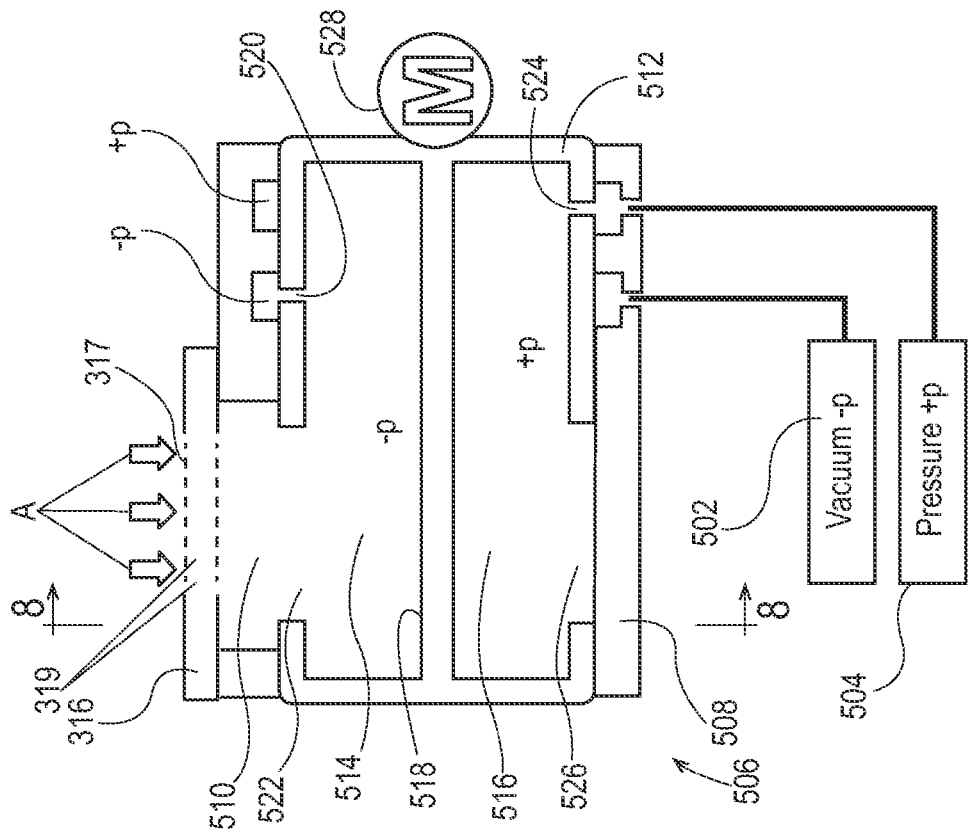
FIG. 7A is a cross sectional view of a pneumatic system operably connected with the first carrier in a first mode of operation from FIG. 6 taken along line 7-7.
Figure 8A:
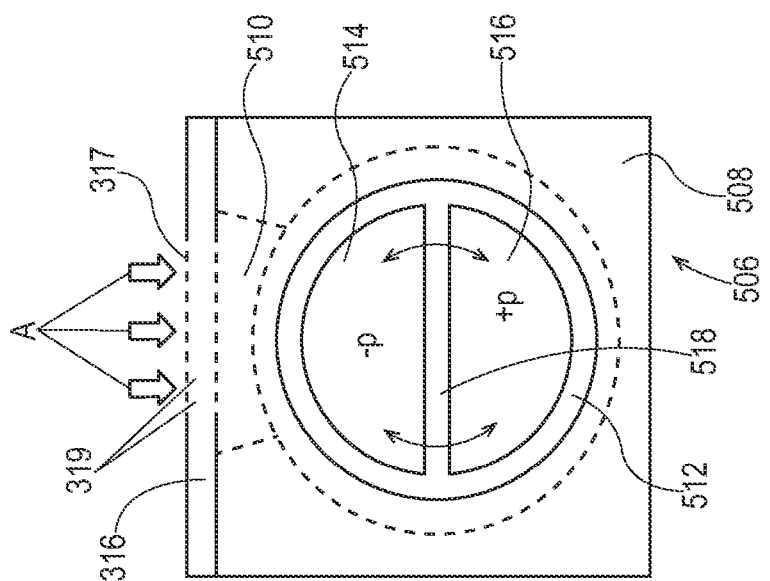
FIG. 8A is a cross sectional view of the rotary valve assembly from FIG. 7A taken along line 8-8.
Figure 7B:
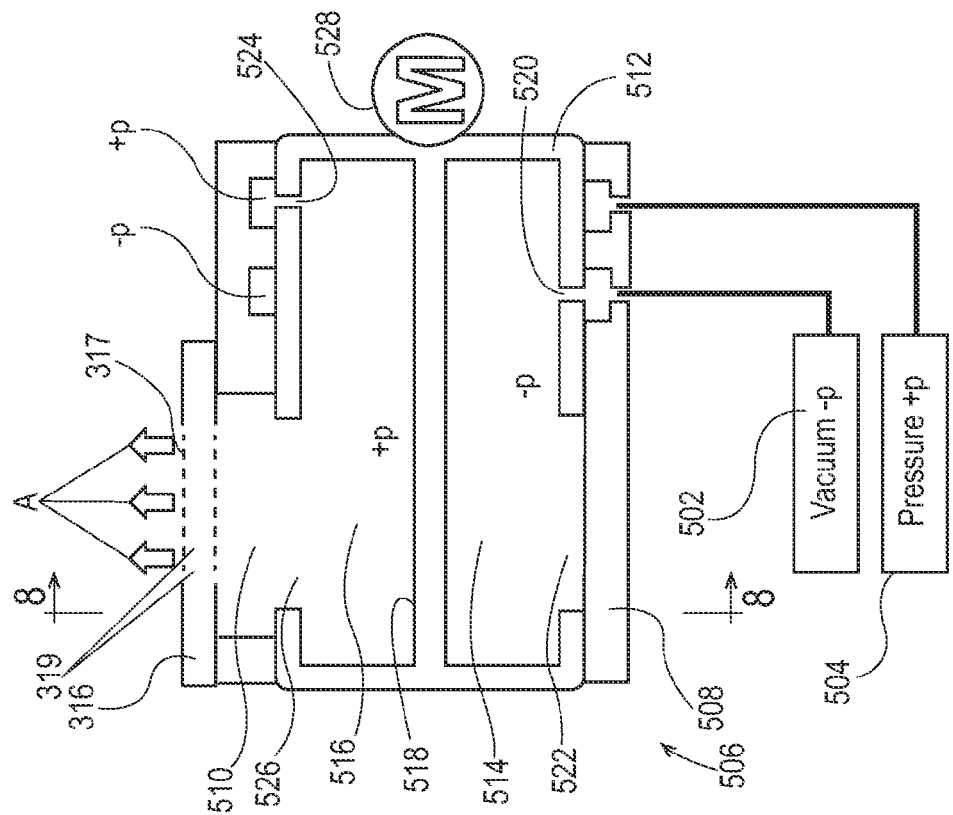
FIG. 7B is a cross sectional view of the pneumatic system operably connected with the second carrier in a first mode of operation from FIG. 6 taken along line 7-7.
Figure 8B:
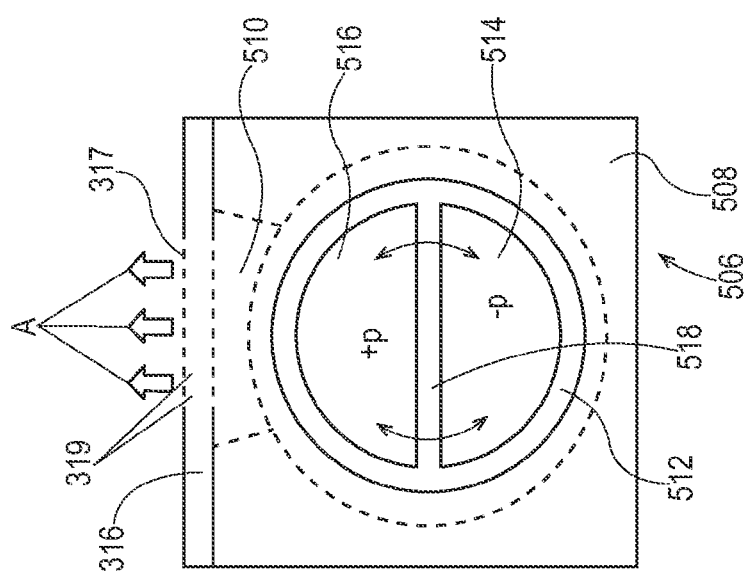
FIG. 8B is a cross sectional view of the rotary valve assembly from FIG. 7B taken along line 8-8.

For example, FIG. 6 provides a schematic illustration of a pneumatic system 500 fluidly connected with the first carrier 316. The pneumatic system 500 includes a vacuum system 502 and a positive pressure system 504. The vacuum system 502 is configured to create a vacuum pressure (−p) that is less than atmospheric pressure. As such, when the vacuum system 502 is fluidly connected with the carrier surface 317 of the first carrier 316, air A is drawn toward and through the apertures 319 in the carrier surface 317 such as shown in FIGS. 7A and 8A, creating a suction force that helps hold diapers 100 onto the carrier surface 317. The positive pressure system 504 is configured to create a positive pressure (+p) that is greater than atmospheric pressure. As such, when the positive pressure system 504 is fluidly connected with the carrier surface 317 of the first carrier 316, air A is forced through and from the apertures 319 in the carrier surface 317 such as shown in FIGS. 7B and 8B, creating a pushing or blow-off force that helps push the diapers 100 away from the carrier surface 317.

In the configuration shown in FIG. 6, the vacuum system 502 is configured to provide a continuous suction pressure to a first zone or length 317a of the carrier surface 317 of the first carrier 316. The vacuum system 502 and pressure system 504 are also connected with a rotary valve assembly 506 that is operable to fluidly connect the vacuum system 502 or the pressure system 504 with a second zone or length 317b of the carrier surface 317 of the first carrier 316. Although a rotary valve assembly configuration is discussed herein, it is to be appreciated that various types of valve configurations can be used. The first zone 317a may be upstream of the second zone 317b, and the second zone 317b may be downstream of the first zone 317a. Further, the transition from the first zone 317a to the second zone 317b may be in the pick-up zone 332, upstream of the pick-up zone 332, or downstream of the pick-up zone 332. As shown in FIGS. 7A-8B, the valve assembly 506 may include a valve body 508 having an opening 510 fluidly connected with the carrier surface 317 of the first carrier 316. The valve body 508 is also fluidly connected with the vacuum system 502 and the positive pressure system 504. The valve body 508 houses a valve insert 512 having a first chamber 514 and a second chamber 516 separated from each other by a wall 518. The first chamber 514 may include a first port 520 and a second port 522, and the second chamber 516 may include a first port 524 and a second port 526.

As shown in FIGS. 7A-8B, the valve insert 512 may be connected with an actuator 528 adapted to rotate or pivot the valve insert 512 inside the valve body 508 to selectively place the vacuum system 502 and the pressure system 504 in fluid communication with the carrier surface 317 of the first carrier 316. For example, the actuator 528 may rotate the valve insert 512 to a first position such as shown in FIGS. 7A and 8A to place the vacuum system 502 in fluid communication with the carrier surface 317 of the first carrier 316. When the valve insert 512 is placed in the first position, the pneumatic system 500 is in a first mode of operation wherein the vacuum system 502 is in fluid communication with the carrier surface 317 along the first zone 317a and the second zone 317b. More particularly, as shown in FIGS. 7A and 8A, the first port 520 of the first chamber 514 is placed in fluid communication with the vacuum system 502, and the second port 522 of the first chamber 514 is placed in fluid communication with the opening 510 in the valve body 508. Thus, in the first position, the vacuum system 502 draws air A toward and through apertures 319 in the carrier surface 317, through opening 510 in the valve body 508, and through the second port 522 into the first chamber 514. The air is also drawn from the first chamber 514 through the first port 520 and to the vacuum system 502. As the vacuum system draws air into the apertures 319 in the carrier surface 317, a suction force is created that helps hold diapers 100 in position on the carrier surface 317.

It is to be appreciated that actuator 528 may be configured in various ways. For example, in some embodiments, the actuator 528 may be provided in the form an electromechanical solenoid; servomotor; pneumatic cylinder; or hydraulic cylinder and may include linkage mechanisms, such as gears, to redirect output motion of the actuator in line with the required direction of motion of the valve insert.

As shown in FIGS. 7B and 8B, the actuator 528 may also rotate the valve insert 512 to a second position to place the positive pressure system 504 in fluid communication with the carrier surface 317 of the first carrier 316. When the valve insert 512 is placed in the second position, the pneumatic system 500 is in a second mode of operation wherein the vacuum system 502 is in fluid communication with the carrier surface 317 along the first zone 317a, and the positive pressure system 504 is in fluid communication with the second zone 317b. More particularly, as shown in FIGS. 7B and 8B, the first port 524 of the second chamber 516 is placed in fluid communication with the vacuum system 502, and the second port 526 of the second chamber 516 is placed in fluid communication with the opening 510 in the valve body 508. Thus, in the second position, the positive pressure system 504 forces air through first port 524 and into the second chamber 516 of the valve insert 512. From the second chamber 516, the air A is forced through the second port 526, through the opening 510 in the valve body 508; and through and away from the carrier surface 317. As the positive pressure system forces air through the carrier surface 317, a blow-off or pushing force is created away from the carrier surface 317 that helps remove diapers 100 from the carrier surface 317. As discussed below, the actuator 528 may be operably connected with an inspection system to rotate the valve insert 512 to the first position shown in FIGS. 7A and 8A in response to a reject command from the inspection system to remove defective diapers 100R from the converting process.

Figure 11:
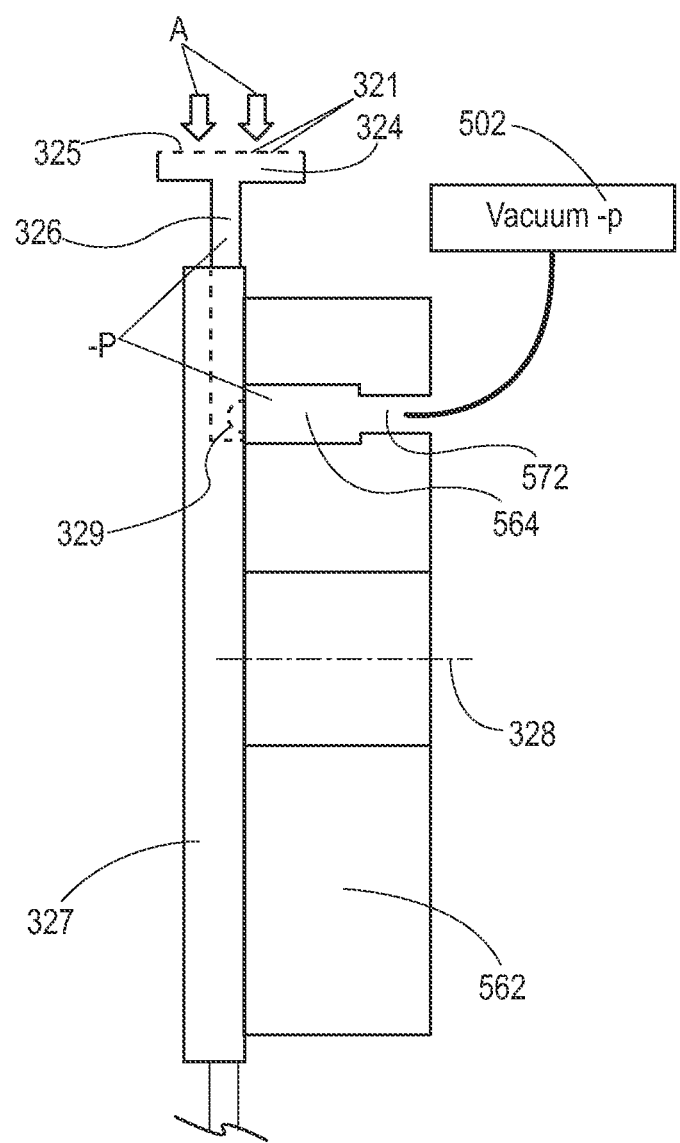
FIG. 11 is a cross sectional view of a pneumatic system and manifold valve assembly operably connected with the transfer apparatus from FIG. 9 taken along line 11-11.

FIG. 6 also provides a schematic illustration of a pneumatic system 550 operably connected with the carrier members 324 of the transfer apparatus 320. The pneumatic system 550 includes a vacuum system 552 and a positive pressure system 554. The vacuum system 552 is configured to create a vacuum pressure (−p) that is less than atmospheric pressure. As such, when the vacuum system 552 is fluidly connected with the carrier surface 325 of the carrier member 324, air A is drawn toward and through apertures 321 in the carrier surface 325 such as shown in FIGS. 10A and 11, creating a suction force that helps hold diapers 100 onto the porous surface 325. The positive pressure system 554 is configured to create a positive pressure (+p) that is greater than atmospheric pressure. As such, when the positive pressure system 554 is fluidly connected with the porous surface 325 of the carrier member 324, air A is forced through and from apertures 321 in the carrier surface 325 such as shown in FIG. 10B, creating a pushing or blow-off force that helps push the diapers 100 away from the carrier member 324.

In the configuration shown in FIG. 6, the vacuum system 552 and the pressure system 554 are connected with a manifold valve assembly 556 that is operable to selectively fluidly connect the vacuum system 552 or the pressure system 554 with the carrier surfaces 325 of carrier members 324 over a first portion 558 of the orbital path defined by the carrier members 324 around the first axis of rotation 328. The vacuum system 552 is also configured to provide a continuous suction pressure to the carrier surfaces 325 of carrier members 324 over a second portion 560 of the orbital path defined by the carrier members 324 around the first axis of rotation 328.

As shown in FIGS. 6-11, the support members 326 of the transfer apparatus 320 may extend radially outward from a rotor member 327 adapted to rotate around the first axis of rotation 328. The support members 324 may also include openings 329 in fluid communication with the carrier surfaces 325 of the carrier members 324. As such, air A can flow in and out of apertures 321 in the carrier surface 325, through the support member 326, and in and out of the opening 329, such as shown in FIGS. 10A and 10B. As discussed below, as the rotor member 327 rotates around the first axis of rotation 328, the openings 329 may be placed in fluid communication through a stator member, referred to herein as a manifold stator 562, with vacuum system 552 and/or positive pressure system 554 in the first zone 558 and second zone 560.

Figure 9:
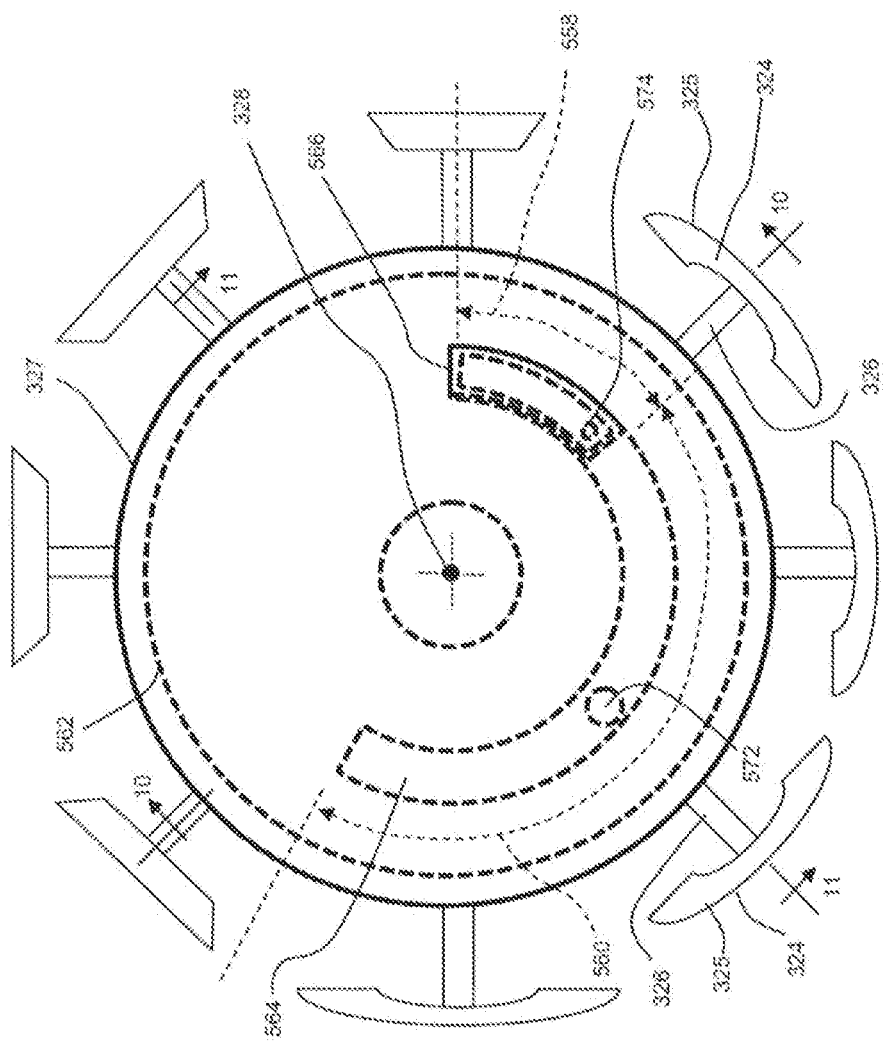
FIG. 9 a schematic view of a manifold valve assembly operably connected with the transfer apparatus from FIG. 6.

As shown in FIGS. 9-11, the manifold stator 562 is stationary and is positioned adjacent the rotor member 562. The manifold stator 562 includes an arcuate manifold 564 that is fluidly connected with the openings 329 of the support members 326 as the rotor member 562 rotates the support members 326 and associated carrier members through the first zone 558 and second zone 560. The manifold stator is also operably connected with the manifold valve assembly 556. More particularly, the manifold valve assembly 556 includes a manifold insert 566 connected with an actuator 568. The manifold insert 566 is arcuately shaped and extends along and inside a portion of the length of the manifold 564. And the manifold insert is movably and/or slidably connected with the manifold 564. The actuator 568 selectively moves the manifold insert 566 back and forth between first and second positions, V and P, respectively, within the manifold 564, as shown in FIGS. 10A and 10B. As shown in FIG. 9, the portion of the manifold 564 housing the manifold insert 566 corresponds with the first zone 558, and the remaining portion of the manifold 564 that does not house the manifold insert 566 corresponds with the second zone 560.

It is to be appreciated that actuator 568 may be configured in various ways. For example, in some embodiments, the actuator 568 may be provided in the form an electromechanical solenoid; servomotor; pneumatic cylinder; or hydraulic cylinder and may include linkage mechanisms, such as gears, to redirect output motion of the actuator in line with the required direction of motion of the valve insert.

With continued reference to FIGS. 9-11, the positive pressure system 554 is fluidly connected with the manifold stator 562 through a first port 570, and the vacuum system 552 is fluidly connected with the manifold stator 562 through a second port 572. The actuator 568 moves the manifold insert 566 back and forth to selectively place the positive pressure system 554 in fluid communication with a portion of the manifold 564 corresponding with the first zone 558. More particularly, the manifold insert includes an opening 574 that is selectively placed in fluid communication with the first port 570 in the manifold stator 562 depending on the position of the manifold insert 566. For example, in FIG. 10A, the actuator 568 has moved the manifold insert 566 into a first position V. In position V, the manifold insert 566 covers or blocks the first port 570. In contrast, as shown in FIG. 10B, the actuator 568 has moved the manifold 566 into a second position P. In position P, the manifold insert 566 does not block the first port 570. As such, pressurized air can flow from the positive pressure system 554 through the first port 570 and the opening 574 in the manifold insert and into a portion of the manifold 564 corresponding with arcuate length of the manifold insert 566. As shown in FIGS. 9 and 11, the vacuum system 552 provides a continuous vacuum pressure (−p) to the portion of the manifold 564 that does not house the manifold insert 566. And when the manifold insert 566 is in position V, such as shown in FIG. 10B, the vacuum system 552 provides a vacuum pressure (−p) to the portion of the manifold 564 that houses the manifold insert 566.

Although the actuator 568 is described above as moving the manifold insert 566 back and forth to selectively place the positive pressure system 554 in fluid communication with a portion of the manifold 564 corresponding with the first zone 558, it is to be appreciated that additional configurations are contemplated. For example, the actuator 568 may be configured to move the manifold insert 566 to block the fluid communication of the vacuum system 552 with a portion of the manifold 564, and a solenoid may be used to selectively place the positive pressure system 554 in fluid communication with a portion of the manifold 564.

As shown in FIGS. 9, 10A, and 11, when the manifold insert 566 is in position V, the vacuum system applies a suction pressure along the entire length of the manifold 564, including the first zone 558 and the second zone 560. As the rotor member 327 rotates and moves the openings 329 in the support members 326 along the length of the manifold 564, the vacuum system 552 draws air A into apertures 321 in the carrier surface 325 of the carrier member 324, through the support member 326 and manifold 324, and from the second port 572 in the manifold stator 562. As such, the pneumatic system 550 may be placed in a first mode of operation when the manifold insert 566 is in position V, wherein the vacuum system 552 applies a suction force to help hold diapers 100 on the carrier members 324 through the first zone 558 and the second zone 560.

As shown in FIGS. 9, 10B, and 11, when the manifold insert 566 is in position P, positive pressure system 554 applies a positive pressure (+p) along the length of the manifold 546 corresponding with the first zone 558. And the vacuum system applies a suction pressure (−p) along the length of the manifold 564 corresponding with the second zone 560. Thus, as the rotor member 327 rotates and moves the openings 329 in the support members 326 along the length of the manifold 564 corresponding with the first zone 558, the positive pressure system 554 forces air to flow into the first port 570 in the manifold stator 562, through the opening 574 in the manifold insert 566, into the portion of the manifold 564 corresponding with the first zone 558. Pressurized air then flows from the manifold through the support member 326 and air A exits from apertures 321 in the carrier surface 325 of the carrier member 324. As such, the pneumatic system 550 may be placed in a second mode of operation when the manifold insert 566 is in position P, wherein the positive pressure system 554 applies a blow-off or pushing force to help push diapers 100 away from the carrier members 324 in the first zone 558.

As discussed below, the actuator 568 may be operably connected with an inspection system to move the manifold insert 566 into position P in response to a reject command from the inspection system to remove defective diapers 100R from the converting process.

As previously mentioned, the methods and apparatuses 300 herein may also utilize inspection systems and processes for detecting and monitoring defective absorbent articles 100 during the manufacturing process. An embodiment of an inspection system 600 is schematically represented in FIG. 4. As discussed in more detail below, the inspection systems and methods may utilize feedback from technologies, such as vision systems, sensors, communication networks, and controllers. In some embodiments, the inspection systems may be configured to alarm and/or record occurrences of defective products during the manufacturing processes as well as remove defective products from the manufacturing process.

In some embodiments, the inspection system 600 may detect and/or track missing or defective components and/or substrates through the manufacturing process. The inspection system 600 may also correlate inspection results from such defective components and/or substrates to absorbent articles 100 made therefrom. In turn, the inspection system 600 may be used to control a pneumatic system on the carrier apparatus 320, wherein defective absorbent articles 100R are rejected. In some configurations, defective articles 100R may be removed from the process, such as shown in FIG. 4, wherein defective diapers 100R are removed from carrier members 324 while traveling from the pick-up zone 332 and directed a reject bin 336. Diapers 100 that are not deemed to be defective may be transferred to the drop-off zone 332 and subject to further processing steps.

It is to be appreciated that the term "reject bin" is used herein generically to designate the location where rejected diapers may be conveyed. As such, the reject bin 336 may include various systems. For example, the reject bin may 336 may include systems such as conveyors and/or pneumatic systems to provide additional transport or conveyance of rejected diapers to other locations.

As shown in FIG. 4, the inspection system 600 may include a sensor 602 operatively connected with a controller 604. Various types of sensors 602 and other devices may be arranged adjacent the apparatus 300 and may communicate with the controller 604. Based on such communications, the controller 604 may monitor and affect various operations on the apparatus 300. As discussed in more detail below, for example, the controller 604 may send reject commands 1000 to affect operation of the pneumatic system 500 operably connected with the first carrier 316 and/or the pneumatic system 550 operably connected with the transfer apparatus 320 based on communications with the sensor 602.

It is to be appreciated that various types of controller and sensor configurations may be utilized with the inspection system 600, such as for example, disclosed in U.S. Pat. No. 8,145,338. For example, the controller 604 may include a computer system, which may, for example, include one or more types of programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators.

It is to be appreciated that various different types of inspection sensors 602 may be used to monitor substrates and various components. For example, inspection sensors 602 may be configured as photo-optic sensors that receive either reflected or transmitted light and serve to determine the presence or absence of a specific material; metal-proximity sensors that use electromagnetic to determine the presence or absence of a ferromagnetic material; or capacitive or other proximity sensors using any of a number of varied technologies to determine the presence or absence materials. Inspection sensors 602 may also be configured as vision systems and other sub-processing devices to perform detection and, in some cases, logic to more accurately determine the status of an inspected product. Particular examples of such inspections sensors 602 may include Cognex Insight, DVT Legend or Keyence smart cameras, component vision systems such as National Instruments PXI or PC based vision system such as Cognex VisionPro or any other vision system software which can run on a PC platform.

As previously mentioned, the inspection sensors 602 may detect missing, misplaced, and/or defective and/or damaged components and/or substrates used in assembling absorbent articles 100. It is also to be appreciated that the inspection sensors 602 may be configured to perform various functions in the inspection system 600. For example, the sensors may be configured to detect defects within substrates and/or components themselves, such as for example, damage, holes, tears, dirt, and the like, and may also detect defective assemblies and/or combinations of the substrates and components, such as for example, missing and/or misplaced elastic material and the like. As such, inspection sensors may be configured to detect the presence or absence of substrates and/or components, and may be configured to detect the relative placement of substrates and/or components. As discussed in more detail below, based on the detections of the inspection sensors 602, feedback signals from the inspection sensors in the form of inspection parameters 1000 are communicated to the controller 604.

It should also be appreciated that inspection parameters 1000 may be provided from inspection sensors 602 in various forms. In some configurations, inspection parameters 1000 may be in the form of "results," such as for example, provided from a sensor state change resulting in a binary input corresponding with the detected presence or absence of a defect, such as for example, the presence or absence of components and/or substrates. For example, inspection parameters 1000 may indicate the presence or absence of discrete bond regions 406; and side seams 178, 180. In other examples, an inspection parameter 1000 may indicate the presence or absence of a tear, hole, splice tape, and/or contaminants in the first and second elastic belt substrates 402, 404 and/or chassis 102.

In still other examples, the inspection sensors 602 may be configured to detect improperly cut and/or uncut absorbent articles 100. For example, in some configurations, inspection sensors 602 may include a proximity sensor that detects the position of a loading system, such as an air cylinder, for the cutting apparatus 306. Such a proximity sensor may be configured to detect various operating conditions with respect to the cutting apparatus 306, such as for example, an operating condition that results from the knife roll 308 being unexpectedly unloaded. Such a condition may be caused, for example, by a misplaced absorbent core 142 that advances between the knife roll 308 and anvil roll 310 that causes the knife roll 308 to be displaced from the anvil roll 310. As a result of the knife roll displacement, some absorbent articles 100 may not be cut or may be improperly cut by the cutting apparatus 306. Thus, feedback from the proximity sensor could be used by the inspection system 500 to issue a reject command and prevent the transfer apparatus 320 from transferring the uncut and/or improperly cut absorbent articles 100R without having to stop the entire converting process to remove the defective articles.

In some embodiments, inspection parameters 1000 may be provided in the form of measurements and/or numerical indications of detected positions of elastic material and/or substrates; numerical indications of the positions of elastic material and/or substrates relative to other elastic materials and/or substrates; and/or numerical indications of the positions of elastic materials and/or substrates relative to another physical or virtual reference. For example, inspection parameters 1000 may indicate the relative position of one feature of an absorbent article, such as an outer lateral edge 107*a*, 109*a* of an elastic belt 106, 108, with respect to an elastic strand 168. In other embodiments, inspection parameters 1000 may be in the form of images transferred via a standard protocol such as ftp (File Transfer Protocol), DDE (Dynamic Data Exchange), or OPC (Object Linking and Embedding for Process Control), which are stored in a database or stored in a specified directory on an image server for the purpose of either operator visualization, offline image processing or claim support.

As shown in FIG. 4, the inspection sensors 602 may be connected with the controller 604 through a communication network 606, which allows the inspection sensors 602 to communicate inspection parameters 1000 to the controller 604. The inspection sensors 602 and the controller 604 may be connected directly with the communication network 606. Such sensors may include, for example, vision systems such as National Instruments CVS or any PC-based vision system such as Cognex VisionPro. Such sensors may also include other controllers that may be configured as peers to the controller or may be configured as subordinate to the controller. In some embodiments, the inspection sensors 602 may be indirectly connected with the communication network 606. For example, the inspections sensors 602 may be connected with the communication network 606 through a remote input and output (I/O) station, such as discussed in U.S. Patent Publication No. 2010/0305740A1. When utilizing remote I/O stations, the inspection sensors 602 may be hardwired to the remote I/O stations, and in turn, the remote I/O stations may be connected with the communication network 606. Example remote I/O stations or other IEEE-1588 based instruments that can be utilized with systems and methods herein include, for example a National Instruments PCI-1588 Interface (IEEE 1588 Precision Time Protocol Synchronization Interface) that synchronizes PXI systems, I/O modules and instrumentation over Ethernet/IP or a Beckhoff Automation EtherCat and XFC technology (eXtreme Fast Control Technology).

In some embodiments, the inspection sensors 602 may communicate inspection parameters 1002 to the controller 604. In some instances, the inspection parameter 1002 may provide an indication of a defect in a substrate and/or component and/or defective assemblies and/or combinations of the substrates and components used to make absorbent articles 100. It is to be appreciated that the inspection system 600 may include inspection sensors 602 that monitor various locations of the manufacturing process in addition to the locations shown in FIG. 4. The detected defect may be tracked during the manufacturing process and correlated with a defective absorbent article 100R. In turn, the controller 604 of the inspection system 600 may send a reject command 1000 to one or more components of the converting apparatus 300, such as one or more pneumatic systems 500, 550, to remove the defective article 100R from the manufacturing process.

As previously mentioned, the inspection system 600 may be utilized with the apparatuses and methods 300 herein to detect and monitor defects during the manufacturing process. For example, as shown in FIG. 4, the sensor 602 monitors the continuous length of absorbent articles 400 advancing from the bonder 304. As such, the sensor 602, 602*a* in FIG. 4 may be configured to inspect and/or detect the quality and/or locations of the discrete bond regions 406, such as shown in FIG. 5B. Inspection sensors 602, 602*b* may also be located between the cutting apparatus 306 and the transfer apparatus 320. As such, the sensors 602 may be configured to monitor components and substrates combined to create the continuous length of absorbent articles 400 in various stages of the assembly process and/or monitor the quality and/or location of the cuts made by the cutting apparatus 306.

With continued reference to FIG. 4, the inspection system 600 may also correlate inspection results and measurements from defective substrates and components to defective absorbent articles 100R made therefrom. In turn, the inspection system 600 may be used to control an apparatus or system, wherein defective absorbent articles 100R are rejected. In some configurations, the controller 604 of the inspection system 600 may send a reject command 1000 to the pneumatic system 500 operably connected with the first carrier 316 and/or the pneumatic system 550 operably connected with the transfer apparatus 320, which in turn, removes defective articles 100R from the process, such as shown in FIG. 4. In some embodiments, defective diapers 100R may be redirected from the manufacturing process to a reject bin 336. Diapers 100 that are not deemed to be defective may be subject to further processing steps, such as folding and packaging.

It is to be appreciated that the inspection system 600 may operate in conjunction with elements of the converting apparatus 300 in various ways. For example, various components of the pneumatic systems 500, 550, first carrier 316, and/or transfer apparatus 320 may be adapted to operate in various ways in response to a reject command 1000 to remove defective diapers 100R from the manufacturing process.

As discussed above, absorbent articles 100 may be transferred from the first carrier 316 to a carrier member 324 on the transfer apparatus 320. A pneumatic system 550 including a vacuum system 552 and a positive pressure system 554 may also be operably connected with the transfer apparatus 320 as described above with reference to FIGS. 6 and 9-11. As such, in a first mode of operation, the vacuum system 552 exerts a suction force to help hold the diapers 100 in position on the carrier members 324 while moving from the pick-up zone 332, through the first zone 558 and second zone 560, and to the drop-off zone 334. In some embodiments, a reject command 1000 may be operable place the pneumatic system in a second mode of operation, such as for example, by operating the actuator 568 to move the manifold insert 566 into position P. As such, the positive pressure system 554 applies a blow-off or pushing force to help push the defective diapers 100R away from the carrier members 324 in the pick-up zone 332 and/or first zone 558. After the defective diapers 100R are rejected, the inspection system 600 may then return the pneumatic system to the first mode of operation. It is to be appreciated the inspection system 600 and pneumatic system 550 may be operable to reject defective diapers 100R by placing the pneumatic system 550 into the second mode of operation before the defective diapers 100R are transferred to the carrier members 324 in the pick-up zone 332. Thus, positive pressure system 554 may prevent defective diapers 100R from being transferred to the carrier member 324, and may instead be forced away from the transfer apparatus 320 toward the reject bin 336. In some embodiments, the inspection system 600 and pneumatic system 550 may be operable to reject defective diapers 100R by placing the pneumatic system 550 into the second mode of operation after the defective diapers 100R are transferred to the carrier members 324 in the pick-up zone 332. Thus, positive pressure system 554 remove defective diapers 100R the carrier member 324 in for example, the first zone 558, and may be directed away from the transfer apparatus 320 toward the reject bin 336.

In some embodiments, the pneumatic system 550 may not include a positive pressure system 554. As such, a reject command 1000 may be operable to only prevent the vacuum system from applying a suction force to defective diapers 100R in the pick-up zone 332. Thus, defective diapers 100R may not be transferred to the carrier member 324, and may instead fall away from the transfer apparatus 320 toward the reject bin 336. In some embodiments, in response to a reject command 1000, the vacuum system may be adapted to cease applying a suction force to a defective diaper 100R that has been picked up by a carrier member 324 before being transferred to the drop-off zone 334. As such, the defective diaper 100R is no longer held to the carrier member 324 by the vacuum system. Centrifugal force resulting from the rotational motion of the transfer apparatus 320 may separate the defective diaper 100R from the moving carrier member 324.

In some embodiments, a pneumatic system 500 including a vacuum system 502 and a positive pressure system 504 may also be operably connected with the first carrier 316 as described above with reference to FIGS. 6-8B. In the second mode of operation discussed above with reference to FIGS. 4, 6, 7B and 8B, the vacuum system 502 is in fluid communication with the carrier surface 317 along the first zone 317a, and the positive pressure system 504 is in fluid communication with the second zone 317b. The transition from the first zone 317a to the second zone 317b may be located in the pick-up zone 332. As such, the vacuum system 502 applies a suction force to the diapers 100 to help hold the diapers 100 on the carrier surface 317 of the first carrier 316 while advancing to the pick-up zone 332. While advancing to the second zone 317b at the pick-up zone 334, the positive pressure system 504 may apply a blow-off force to push the diapers 100 away from the carrier surface 317 of the first carrier 316 and toward a carrier member 324 moving through pick-up zone 334.

In some embodiments, a reject command 1000 may be operable place the pneumatic system 500 in the first mode of operation discussed above with reference to FIGS. 4, 6, 7A, and 8A, such as for example, by operating the actuator 528 to rotate the valve insert 566 into the first position. Thus, is the first mode of operation, the vacuum system 502 is in fluid communication with the carrier surface 317 along the first zone 317a and second zone 317b. As such, the vacuum system 502 applies a suction force to hold the defective diaper 100R on the first carrier 316 as the diaper 100R advances past the pick-up zone and into the second zone 317b. Thus, a reject command 1000 may be configured to be operable to maintain suction pressure to hold the defective diaper 100R on the first carrier 316, allowing the first carrier 316 to advance the defective diaper 100R past the pick-up zone 332. Once past the pick-up zone, the reject command 1000 may be operable to place the pneumatic system back into the second mode of operation, reengaging the positive pressure system 504, to blow or push the defective diaper away from the carrier surface 317 of the first carrier 316 in the second zone 317b toward the reject bin 336. In some embodiments, the defective diaper 100R is held to the first carrier 316 by suction forces until advance beyond the end of the second zone 317b, wherein the defective diaper falls is no longer held with suction forces and falls away from the carrier surface 317 of the first carrier to the reject bin 336.

As shown in FIG. 4, the reject bin 336 may also be located below the first carrier 316, the pick-up zone 316, and/or the transfer apparatus 320, thus gravitational forces may also help guide the defective article 100R downward toward the reject bin 336 after separating from the carrier member 324 and/or first carrier 316. It is also to be appreciated the pneumatic system 500 operably connected with the first carrier 316 and the pneumatic system 550 operably connected with the transfer apparatus 320 may be configured to operate together or individually in various ways in response to a reject command 1000.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for rejecting defective absorbent articles from a web converting manufacturing process, the method comprising the steps of:
   converting a substrate and component parts into a continuous length of absorbent articles;
   inspecting the substrate or at least one component part with a sensor;
   communicating inspection parameters from the sensor to a controller;
   cutting the continuous length of absorbent articles into discrete absorbent articles;
   identifying defective discrete absorbent articles based on the inspection parameters;
   advancing the discrete absorbent articles in a machine direction on a first carrier;
   applying a vacuum pressure to the first carrier to hold the discrete absorbent articles on the first carrier;
   transferring a plurality of the discrete absorbent articles from the first carrier onto carrier members at a pick-up zone proximate the first carrier;
   moving carrier members from the first position proximate the first carrier to a second position proximate a second carrier; and
   transferring the plurality of the discrete absorbent articles from the carrier members to the second carrier at a drop off zone; and
   rejecting the defective discrete absorbent articles before the defective absorbent articles are transferred to the carrier members by advancing the defective discrete absorbent articles on the first carrier past the pick-up zone.

2. The method of claim 1, wherein first carrier comprises a carrier surface and apertures in the carrier surface, and wherein the step of applying a vacuum pressure further comprises placing the apertures in fluid communication with a vacuum system along a length of the first carrier.

3. The method of claim 2, wherein the step of rejecting the defective absorbent articles further comprises maintaining the apertures in fluid communication with the vacuum system.

4. The method of claim 3, wherein the step of rejecting the defective discrete absorbent articles further comprises interrupting the fluid communication between the apertures and the vacuum system downstream of the pick-up zone.

5. The method of claim 4, further comprising the step of placing the apertures in fluid communication with a positive pressure system at the pick-up zone, and wherein the step of rejecting the defective discrete absorbent articles further comprises interrupting the fluid communication between the apertures and the positive pressure system.

6. The method of claim 5, wherein the step of rejecting the defective discrete absorbent articles further comprises placing at least one of the carrier members in fluid communication with the positive pressure system at the pick-up zone proximate the first carrier.

7. The method of claim 1, wherein the first carrier comprises an apertured belt.

* * * * *